United States Patent
Kay

[11] 3,976,051
[45] Aug. 24, 1976

[54] HEAD-POSITIONING SCINTILLATION CAMERA AND HEAD HOLDER THEREFOR

[76] Inventor: Thomas D. Kay, USAFSAM/NGIR, Brooks AFB, Tex. 78235

[22] Filed: Aug. 5, 1975

[21] Appl. No.: 602,041

[52] U.S. Cl. .............. 128/2 A; 248/206 R; 250/451; 269/322; 297/391
[51] Int. Cl.² ............................ A61B 6/00
[58] Field of Search ............... 128/2 A, 2 R, 24 A, 128/133; 269/322, 328; 250/272, 302, 320, 451, 491; 248/15–17, 118, 206 R, 247, 214; 211/72, 105.1, 123, 182; 297/391, 395, 404, 405, 407

[56] References Cited
UNITED STATES PATENTS

| | | | |
|---|---|---|---|
| 2,577,177 | 12/1951 | Anderson | 269/322 |
| 3,601,445 | 8/1971 | Glynias | 297/404 |
| 3,617,742 | 11/1971 | Schulman | 250/491 |
| 3,622,233 | 11/1971 | Blood et al. | 248/118 |
| 3,655,968 | 4/1972 | Moore et al. | 250/451 |
| 3,700,894 | 10/1972 | Counsell | 250/451 |
| 3,743,832 | 7/1973 | Wright | 250/320 |
| 3,769,966 | 11/1973 | Youdin et al. | 128/2 A |
| 3,825,757 | 7/1974 | Barrett et al. | 250/320 |
| 3,851,644 | 12/1974 | Slagle | 269/328 |
| 3,867,634 | 4/1975 | Hounsfield | 250/451 |

FOREIGN PATENTS OR APPLICATIONS

| | | | |
|---|---|---|---|
| 680,862 | 9/1939 | Germany | 248/206 R |

Primary Examiner—William E. Kamm
Attorney, Agent, or Firm—Joseph E. Rusz; Jacob N. Erlich

[57] ABSTRACT

A holder for immobilizing the head of a patient undergoing a vertex brain scan by a Gamma Scintillation Camera, the holder having a uniquely designed shape capable of comfortably supporting the head. In addition, this holder can be both adjustably and removably utilized in combination with the scintillation camera so as to enable the brain scan operation to take place while the patient is in the seated position.

10 Claims, 3 Drawing Figures

FIG. 2
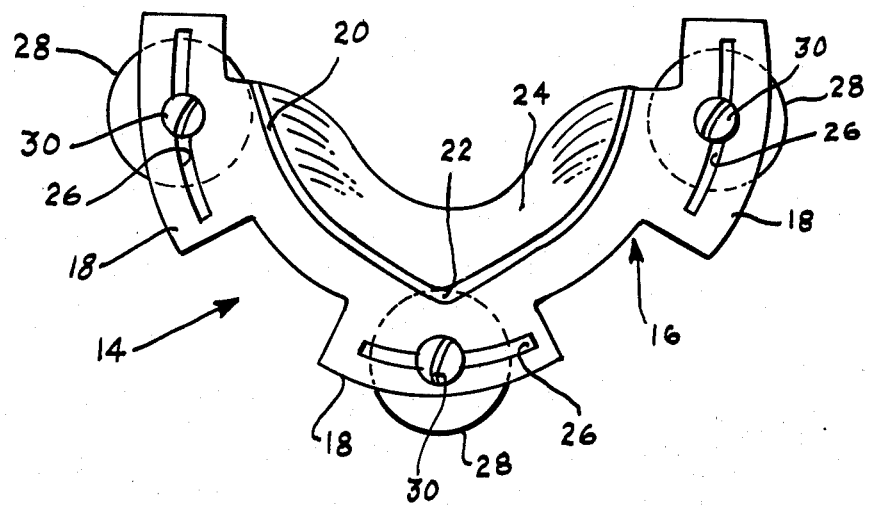
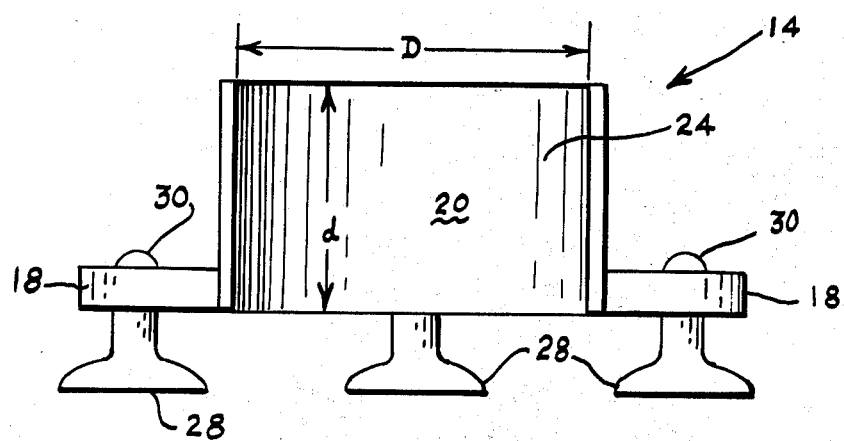
FIG. 3

HEAD-POSITIONING SCINTILLATION CAMERA AND HEAD HOLDER THEREFOR

STATEMENT OF GOVERNMENT INTEREST

The invention described herein may be manufactured and used by or for the Government for governmental purposes without the payment of any royalty thereon.

BACKGROUND OF THE INVENTION

This invention relates generally to scintiphotography, and, more particularly, to a patient head restraining device for the vertex brain scan performed by the Gamma Scintillation Camera during scintiphotography.

Scintiphotography is the diagnostic technique by which both normal and diseased organs within a patient can be studied by following the passage of radioisotopes through the organ. This procedure is performed by the use of a Gamma Scintillation Camera such as Nuclear Chicago's Pho/Gamma HP camera which has the ability to visualize the entire organ of interest at one time and to follow the passage of radioisotopes through the organ. Radiation from the radioisotope is rapidly detected and the position and intensity or the gamma events are produced and displayed in a corresponding position on a cathode ray tube display. Time exposures of the gamma image can be taken thereby providing studies of the organ function in both normal and diseased states. A choice of collimators for various resolution and sensitivity requirements help assure meaningful recordings for most clinical situations.

The Gamma Scintillation Camera System is made up of a gamma detector, assembly for supporting the detector and drive motors and controls for detector orientation. Within the gamma detector is a sodium-ioide thallium activated scintillation crystal. The control console is a desk type assembly which contains an XYZ Analyser, timer, display and power supply.

The counting time required to obtain an optimal image of the emission distribution from a patient using a Gamma Scintillation Camera is determined by the amount of the radioactivity administered, sensor sensitivity, lesion uptake and contrast ratio and the ability of the patient to remain still. The longer the time required for the study, the greater is the probability that significant motion artifacts will occur. Studies show that in organ scans the motion artifacts contribute to the deterioration of the quality of the image after a certain interval of time. For example, it has been found that image quality is good up to three minutes of the scan before motion artifacts reduce the useful information that can be obtained from the increased counting rate. Thus, in order to retain high diagnostic image quality in the longer duration studies, it is critical to device improved patient restraining techniques. Heretofore, these restraining techniques ranged from quite cumbersome apparatus, uncomfortable to the patient, such as sand bags, to extremely complicated apparatus utilized to provide adjustability to a variety of shapes and sizes. In addition many of the prior art restrainers produced gamma backscatter during the scintiphotography procedure.

SUMMARY OF THE INVENTION

The holder of this invention is capable of comfortably immobilizing the head of a patient undergoing a vertex brain scan with a Gamma Scintillation Camera and thereby overcomes the problems set forth in detail hereinabove.

This holder is manufactured from a lightweight low Z number material shaped to conform to the forehead of a patient undergoing the brain scan. In addition the holder of this invention encompasses the features of not only being adjustably and removably mounted on the face of a conventional Gamma Scintillation Camera but also provides a comfortable restrainment for the head of a patient while in the sitting position. Since the vertex brain scan can now be performed with the patient in the sitting position, radiation from the lower body is reduced. Furthermore, the simple construction of this invention continually provides for proper alignment while being easily adaptable to a variety of scintillation cameras. No modification of the existing equipment is necessary in the utilization of the holder of this invention.

It is therefore an object of this invention to provide a holder for the head of a patient which enables a vertex brain scan to be performed while the patient is in the sitting position.

It is a further object of this invention to provide a holder for the head of a patient which elminates any modifications to be provided for on the Gamma Scintillation Camera.

It is another object of this invention to provide a holder for the head of a patient which is capable of removable attachment to a wide variety of scintillation cameras.

It is still another object of this invention to provide a holder for the head of a patient which is economical to produce, and which utilizes conventional, currently available components that lend themselves to standard mass producing manufacturing techniques.

For a better understanding of the present invention together with other and further objects thereof reference is made to the following description taken in conjunction with the accompanying drawing and its scope will be pointed out in the appended claims.

DESCRIPTION OF THE DRAWING

FIG. 2 is a side elevational view of the holder of this invention; and

FIG. 3 is a plan view of the holder of this invention.

DETAILED DESCRIPTION OF THE PREFERRED EMBODIMENT

Figure 1:
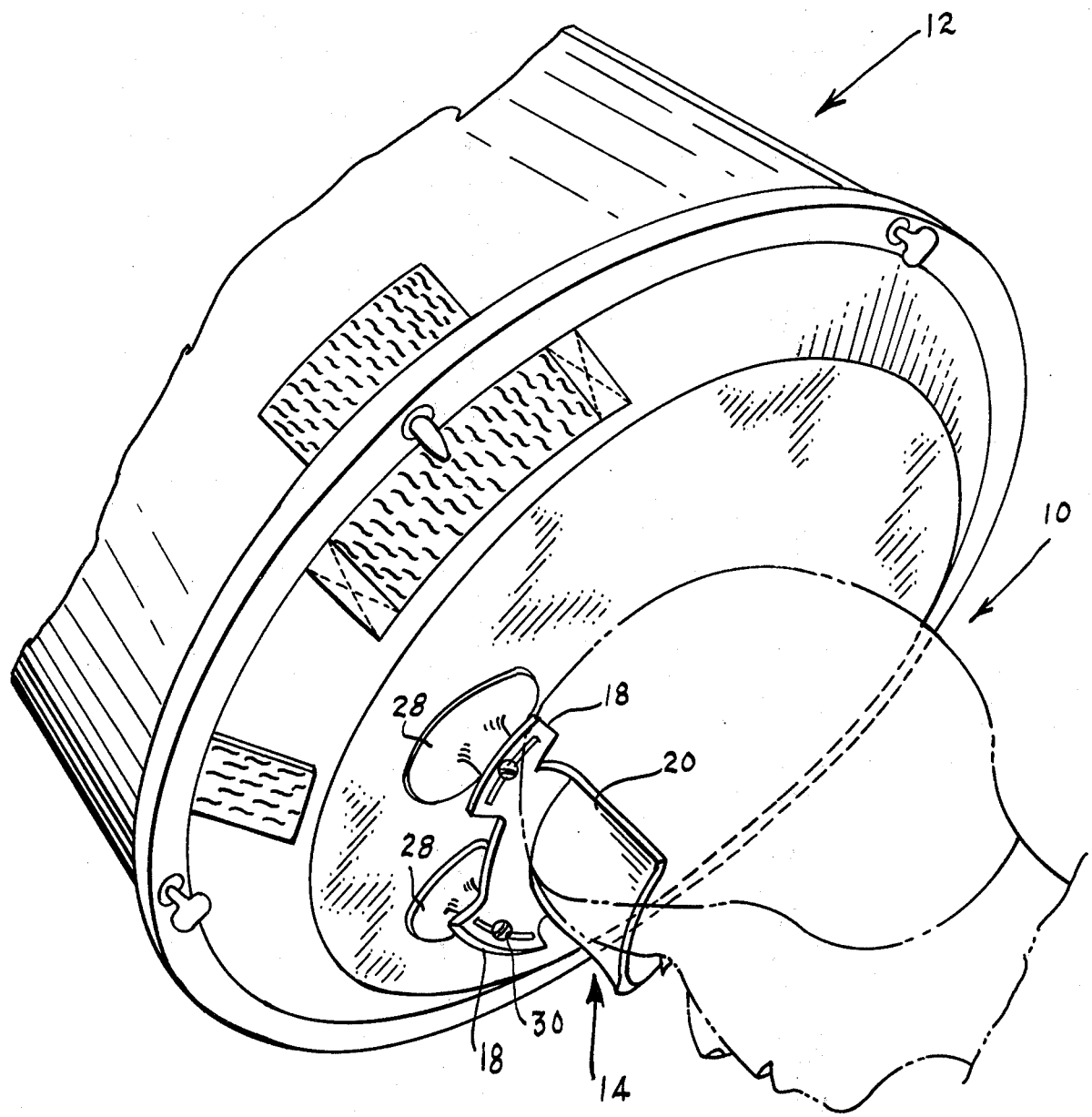
FIG. 1 is a pictorial representation of the holder of this invention restraining and positioning the head of a patient in front of a conventional Gamma Scintillation Camera.

Reference is now made to FIG. 1 of the drawing which shows in pictorial fashion the head 10 of a patient undergoing a vertex brain scan by a conventional Gamma Scintillation Camera 12. The patient's head 10 is held in fixed relationship with respect to camera 12 by the holder 14 of this invention. As shown from FIG. 1 camera 12 is lowered to a 30° position while the seated patient leans forward with his head 10 held in position by holder 14 thereby putting the main portion of the patient's body out of view of camera 12. Holder 14 as shown in FIGS. 1–3 of the drawing is formed of a flat U-shaped base portion 16 having a plurality of protrusions 18 extending from the periphery thereof. Fixedly secured to base portion 16 or forming an integral part thereof is an upstanding substantially U- shaped body 20. Body 20 has an indentation 22 formed in the central base thereof which helps accommodate head 10 of a patient undergoing treatment. Fixedly secured to the interior portion of body 20 is a padded area 24 formed of any suitable material such as vinyl covered foam rubber. This covering adds to the comfort of the patient undergoing treatment.

Reference is still directed to FIGS. 2 and 3 of the drawing which show in detail that protrusions 18 have a slot 26 formed therein to adjustably accommodate any suitable securing member which in this case takes the form of a rubber suction holder 28. Holders 28 are affixed to the front portion of camera 12 as shown in FIG. 1 without destroying the operability of camera 12. Each suction holder 28 is held in place in protrusion 18 by a screw fastener 30 which can be slideably moved along slot 26 thereby accommodating a variety of cameras 12. Once in position the patient can be comfortably aligned with camera 12 in the sitting position in order to undertake lengthy vertex brain scans in comfort. The relationship between the depth, $d$, of the body 20 and the diameter, $D$, of body 20 is $d \cong \frac{1}{2}D$, thereby overcoming any structural problems and eliminating the need for any permanent structural fasteners for holder 14 of this invention. In addition to this criteria, holder 14 is furthermore made of any lightweight low Z number material such as plastic thereby substantially reducing any Gamma scatter radiation associated therewith.

Although this invention has been described with reference to a particular embodiment it will be understood to those skilled in the art that this invention is also capable of a variety of alternate embodiments within the spirit and scope of the appended claims.

I claim:

1. The combination of a holder for the head of a patient undergoing a vertex brain scan and a scintillation camera comprising a plurality of fastening means for removably securing said holder to the face of said scintillation camera, a base portion secured to said fastening means, a U-shaped body extending from said base portion, said body having a concavely-shaped interior configuration for receiving the forehead of a patient and means located within and conformed to fit said interior of said body for comfortably supporting said head of a patient therein whereby said patient may undergo said brain scan in the sitting position.

2. The combination as defined in claim 1 wherein said base portion has a plurality of protrusions extending therefrom and said fastening means are adjustably secured to said protrusions.

3. The combination as defined in claim 2 wherein said body extends a length equal to substantially one-half the diameter thereof from said base portion.

4. The combination as defined in claim 3 wherein said fastening means is in the form of a suction holder slideably mounted within a slot located within each said protrusion.

5. The combination as defined in claim 4 wherein said interior configuration has a centrally located indentation therein.

6. The combination as defined in claim 5 wherein said base portion is of a U-shaped configuration.

7. The combination as defined in claim 6 wherein said holder is made of a lightweight, low Z number material.

8. The combination as defined in claim 7 wherein said material is plastic.

9. A holder for restraining the head of a patient undergoing treatment comprising a U-shaped base portion, a plurality of protrusions extending from said base portion, each of said protrusions having a suction-type fastener adjustably mounted therein, a U-shaped body extending from said base portion, said body having a concavely-shaped interior configuration fitted with a resilient material for comfortably receiving said head of a patient, said body extending from said base portion a length substantially equal to one-half the diameter of said body and said base portion and said body being made substantially of a lightweight, low Z number material.

10. A holder as defined in claim 9 wherein each of said protrusions has a slot therein and said fastener is slideably mounted therein.

* * * * *